United States Patent [19]
Kubota et al.

[11] Patent Number: 5,763,228
[45] Date of Patent: *Jun. 9, 1998

[54] RECOMBINANT ENZYME FOR CONVERTING MALTOSE INTO TREHALOSE FROM PIMELOBACTER SP.

[75] Inventors: Michio Kubota; Keiji Tsusaki; Toshiyuki Sugimoto, all of Okayama, Japan

[73] Assignee: Kabushiki Kaisha Hayashibara Seibutsu Kagaku Kenkyujo, Okayama, Japan

[*] Notice: The term of this patent shall not extend beyond the expiration date of Pat. No. 5,538,883.

[21] Appl. No.: 528,199

[22] Filed: Sep. 14, 1995

Related U.S. Application Data

[63] Continuation-in-part of Ser. No. 485,126, Jun. 7, 1995, abandoned.

Foreign Application Priority Data

Jun. 16, 1994 [JP] Japan ................. 6-156399

[51] Int. Cl.$^6$ ............... C12P 19/12; C12N 9/24; C12N 15/56
[52] U.S. Cl. .......... 435/100; 435/200; 435/320.1; 435/252.33; 435/252.31; 536/23.2
[58] Field of Search ............. 435/100, 200, 435/320.1, 252.3, 252.33, 252.31; 536/23.2

[56] References Cited

U.S. PATENT DOCUMENTS

| | | | |
|---|---|---|---|
| 4,521,252 | 6/1985 | Miyake et al. | 127/46.3 |
| 5,538,883 | 7/1996 | Nishimoto et al. | 435/200 |

FOREIGN PATENT DOCUMENTS

| | | |
|---|---|---|
| 0636693 | 2/1995 | European Pat. Off. |
| 0690130 | 1/1996 | European Pat. Off. |
| 0693558 | 1/1996 | European Pat. Off. |
| 47-13089 | 4/1972 | Japan . |
| 154485 | 12/1975 | Japan . |
| 543938 | 2/1979 | Japan . |
| 56-11437 | 3/1981 | Japan . |
| 56-17078 | 4/1981 | Japan . |
| 5823799 | 8/1981 | Japan . |
| 5872598 | 10/1981 | Japan . |
| 216695 | 2/1982 | Japan . |
| 2106912 | 8/1981 | United Kingdom . |

OTHER PUBLICATIONS

Nishimoto et al. "Existence of a novel enzyme converting Maltose into Trehalose", Bioscience Biotechnology and Biochemistry, vol. 59, No. 11, pp. 2189–2190, 1995.

Tsusaki et al. "Cloning and sequencing of Trehalose Synthase gene from primelobacter sp. R48", Biochimica et Biophysica Acta, vol. 1290, pp. 1–3, 1996.

Nishimoto et al. "Purification and characterization of a thermostable Trehalose Synthase from *Thermus aquaticus*", Bioscience Biotechnology and Biochemistry, vol. 60, No. 5, pp. 835–839, 1996.

Nishimoto et al. "Purification and properties of a novel enzyme, Trehalose Synthase, from Primelobacter sp. R48", Bioscience Biotechnology and Biochemistry, vol. 60, No. 4, pp. 640–644, 1996.

E.M. Southern, Detection of Specific Sequences Among DNA Fragments Seperated By Gel Electrophoresis, J. Mol. Biol. vol. 98, pp. 503–517, 1975.

U.K. Laemmli, Cleavage of Structural Proteins During The Assembly of the Head of Bacteriophage T4, Nature, vol. 227, pp. 680–685, Aug. 15, 1970.

J. Sambrook et al, Molecular Cloning, Cold Spring Harbor Laboratory Press, vols. 1, 2 and 3, 1989.

*Primary Examiner*—Keith D. Hendricks
*Attorney, Agent, or Firm*—Browdy and Neimark

[57] ABSTRACT

A recombinant enzyme, having a molecular weight of about 57,000–67,000 daltons on SDS-PAGE and a pI of about 4.1–5.1 on isoelectrophoresis, which converts maltose into trehalose and vice versa. Depending on the enzymatic conditions, the enzyme forms about 70 w/w % of trehalose when acts on maltose, while about 20 w/w % of maltose when acts on trehalose. The culture of a transformant, prepared by introducing into a host a recombinant DNA containing a DNA coding for the enzyme and a self-replicable vector, facilitates the industrial-scale production of trehalose.

19 Claims, 5 Drawing Sheets

RECOMBINANT ENZYME FOR CONVERTING MALTOSE INTO TREHALOSE FROM PIMELOBACTER SP.

CROSS-REFERENCE TO RELATED APPLICATION

This application is a continuation-in-part of application Ser. No. 08/485,126, filed Jun. 7, 1995, now abandoned, the entire contents of which are hereby incorporated herein by reference.

BACKGROUND OF THE INVENTION

1. Field of the Invention

The present invention relates to a novel recombinant enzyme which converts maltose into trehalose, as well as to a DNA encoding the recombinant enzyme, replicable recombinant DNA, transformant, process for preparing the recombinant enzyme, and enzymatic conversion method of maltose.

2. Description of the Prior Art

Trehalose is a disaccharide which consists of 2 glucose molecules linked together with their reducing groups, and, naturally, it is present in bacteria, fungi, algae, insects, etc., in an extremely-small quantity. Having no reducing residue within the molecule, trehalose does not cause an unsatisfactory browning reaction even when heated in the presence of amino acids or the like, and because of this it can advantageously sweeten food products without fear of causing unsatisfactory coloration and deterioration. Trehalose, however, is far from being readily prepared in a desired amount by conventional methods, and, actually, it has not been scarcely used for sweetening food products.

Conventional methods are roughly classified into 2 groups, i.e. the one using cells of microorganisms and the other employing a multi-enzymatic system wherein enzymes are allowed to act on saccharides. The former, as disclosed in Japanese Patent Laid-Open No. 154,485/75, is a method which comprises allowing to grow microorganisms such as bacteria and yeasts in a nutrient culture medium, and collecting trehalose from the resultant culture. The latter, as disclosed in Japanese Patent Laid-Open No. 216,695/83, is a method which comprises providing maltose as a substrate, allowing a multi-enzymatic system using maltose- and trehalose-phosphorylases to act on maltose, and isolating the formed trehalose from the reaction system. Although the former facilitates the growth of microorganisms without special difficulty, it has a drawback that the resultant culture contains at most 15 w/w % trehalose, on a dry solid basis (d.s.b.). While the latter enables the separation of trehalose with a relative easiness, but it is theoretically difficult to increase the trehalose yield by allowing enzymes to act on substrates at a considerably-high concentration because the enzymatic reaction per se is an equilibrium reaction of 2 different types of enzymes and the equilibrium point constantly inclines to the side of forming glucose phosphate.

In view of the foregoing, the present inventors energetically screened enzymes which directly convert maltose into trehalose, and have found that microorganisms including *Pimelobacter sp.* R48, as disclosed in Japanese Patent Application No. 199,971/88, produce an absolutely novel enzyme which forms trehalose when acts on maltose. This means that trehalose can be prepared from maltose as a material which is readily available in quantity and at low cost, and all the above mentioned objects would be completely overcome thereby. The enzyme productivity of these microorganisms, however, is not sufficient, and this necessitates a considerably-large scale cultivation to obtain an industrial-scale production of trehalose.

Recombinant DNA technology has made a remarkable progress in recent years. At present, even an enzyme, whose total amino acid sequence has not been revealed, can be readily prepared in a desired amount, if a gene encoding the enzyme was once isolated and the base sequence was decoded, by preparing a recombinant DNA containing a DNA which encodes the enzyme, introducing the recombinant DNA into microorganisms or cells of plants or animals, and culturing the resultant transformants. Under these circumstances, urgently required are the finding of a gene which encodes an enzyme capable of forming trehalose from maltose, and the elucidation of the base sequence.

SUMMARY OF THE INVENTION

It is an object of the present invention to provide a recombinant enzyme which forms trehalose when acts on maltose.

It is a further object of the present invention to provide a DNA which encodes the recombinant enzyme.

It is yet another object of the present invention to provide a replicable recombinant DNA containing the DNA.

It is a further object of the present invention to provide a transformant into which the recombinant DNA has been introduced.

It is a further object of the present invention to provide a process for preparing the recombinant enzyme by using the transformant.

It is a further object of the present invention to provide a method for converting maltose into trehalose by the recombinant enzyme.

The first object of the present invention is attained by a recombinant enzyme having the following physicochemical properties of:

(1) Action Forming trehalose when acts on maltose, and forming maltose when acts on trehalose.

(2) Molecular weight About 57,000–67,000 daltons when assayed on sodium dodecyl sulfate polyacrylamide gel electrophoresis (SDS-PAGE); and (3) Isoelectric point (pI) About 4.1–5.1 when assayed on isoelectrophoresis.

The second object of the present invention is attained by a DNA which encodes the recombinant enzyme.

The third object of the present invention is attained by a replicable recombinant DNA which contains the DNA and a self-replicable vector.

The fourth object of the present invention is attained by a transformant obtained by introducing the replicable recombinant DNA into an appropriate host.

The fifth object of the present invention is attained by culturing the transformant in a nutrient culture medium to form the recombinant enzyme, and collecting the formed recombinant enzyme from the resultant culture.

The sixth object of the present invention is attained by an enzymatic conversion method of maltose which contains a step of allowing the recombinant enzyme to act on maltose to form trehalose.

BRIEF DESCRIPTION OF THE ACCOMPANYING DRAWINGS

DETAILED DESCRIPTION OF THE INVENTION

Figure 1:
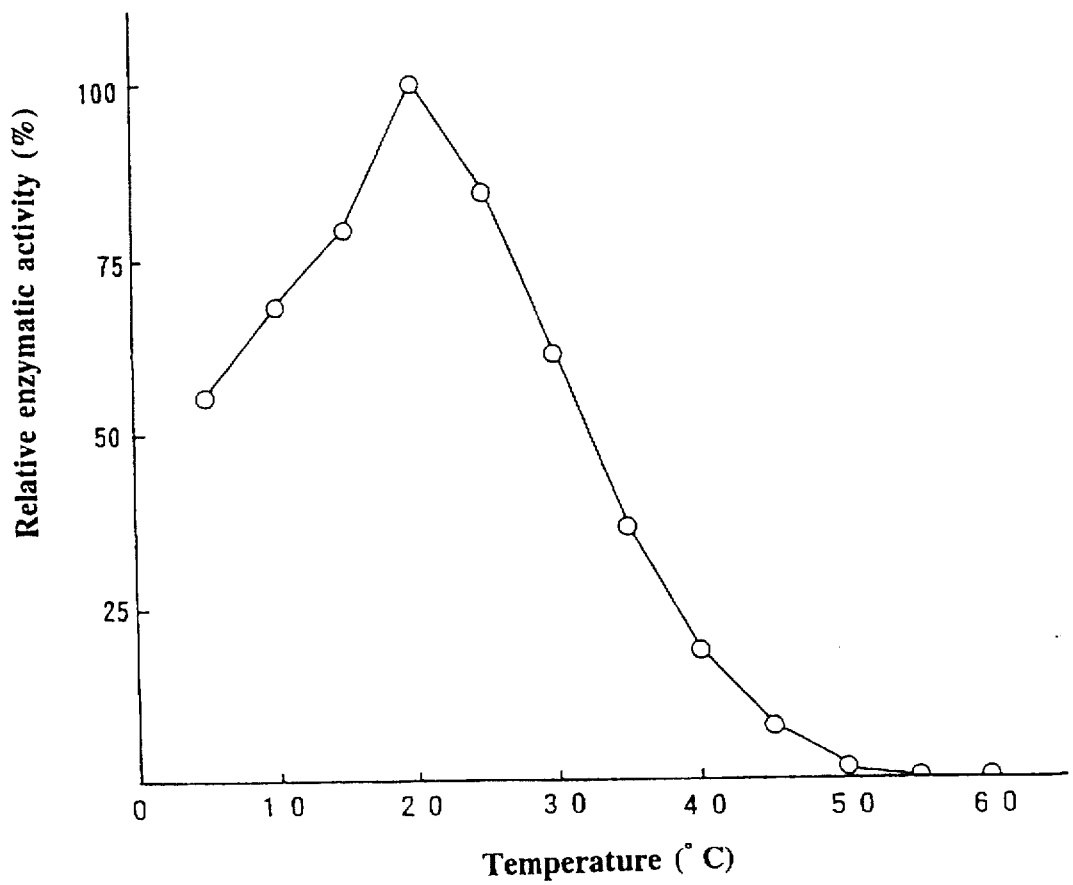
FIG. 1 shows the optimum temperature of an enzyme produced by *Pimelobacter sp.* R48.

The recombinant enzyme according to the present invention forms trehalose when acts on maltose.

The DNA according to the present invention expresses the formation of the present recombinant enzyme by introducing the DNA into an appropriate self-replicable vector to obtain a replicable recombinant DNA which is then introduced into an appropriate host, inherently incapable of forming the recombinant enzyme but readily proliferative, to form a transformant.

The recombinant DNA according to the present invention expresses the production of the recombinant enzyme by introducing the DNA into an appropriate host, which is inherently incapable of forming the recombinant enzyme but readily proliferative, to form a transformant, and culturing the transformant in a nutrient culture medium.

The transformant according to the present invention forms the recombinant enzyme when cultured.

The recombinant enzyme according to the present invention can be formed in a desired amount and with a relative easiness by the process. disclosed in the present specification.

The enzymatic conversion method according to the present invention converts maltose into trehalose with a relative easiness.

Experiments for revealing the physicochemical properties of an enzyme produced by *Pimelobacter sp.* R48 are as follows:

Experiment 1
Purification of Enzyme

Experiment 1-1
Production of Enzyme

In 500-ml Erlenmeyer flasks were placed 100 ml aliquots of a liquid culture medium (pH 7.2) containing 2.0 w/v % glucose, 0.5 w/v % polypeptone, 0.1 w/v % yeast extract, 0.1 w/v % disodium hydrogen phosphate, 0.06 w/v % potassium dihydrogen phosphate, 0.05 w/v % magnesium sulfate heptahydrate, 0.5 w/v % calcium carbonate, and water, and the flasks were autoclaved at 115° C. for 30 min to effect sterilization. After cooling the flasks a seed culture of *Pimelobacter sp.* R48 was inoculated into each flask, followed by the incubation at 27° C. for 24 hours under a rotary-shaking condition of 200 rpm. Twenty L aliquots of a fresh preparation of the same liquid culture medium were put in 30-L jar fermenters and sterilized, followed by inoculating one v/v % of the culture obtained in the above into each liquid culture medium, and incubating the resultant at a pH of 6.0–8.0 and 27° C. for about 40 hours under aeration-agitation conditions.

Thereafter, the enzymatic activity of the resultant culture was assayed to reveal that it contained about 0.55 units/ml of the enzyme. A portion of the culture was centrifuged, and the supernatant was assayed to reveal that it contained about 0.05 units/ml of the enzyme. While the separated cells were suspended in 50 mM phosphate buffer (pH 7.0) to give the initial volume of the portion, followed by assaying the suspension to reveal that it contained about 0.5 units/ml of the enzyme.

Throughout the specification the enzyme activity is expressed by the value measured on the following assay: Place one ml of 10 mM phosphate buffer (pH 7.0) containing 20 w/v % maltose in a test tube, add one ml of an appropriately diluted enzyme solution to the tube, and incubate the solution in the tube at 25° C. for 60 min to effect an enzymatic reaction, followed by further incubation at 100° C. for 10 min to suspend the enzymatic reaction. Thereafter, a portion of the reaction mixture was diluted by 11 times with 50 mM phosphate buffer (pH 7.5), and 0.4 ml of which was placed in a test tube, admixed with 0.1 ml solution containing one unit/ml trehalase, followed by incubating the resultant mixture at 45° C. for 120 min and quantifying the glucose content on the glucose oxidase method. As a control, a system, comprising a trehalase solution and an enzyme solution which has been inactivated by heating at 100° C. for 10 min, is provided and treated similarly as above. The content of the formed trehalose can be estimated based on the glucose content quantified in the above. One unit of the enzymatic activity is defined as the amount which forms one umol trehalose per min under the above conditions.

Experiment 1-2
Purification of Enzyme

The culture obtained in Experiment 1—1 was centrifuged to separate cells, and about 0.5 kg of the wet cells thus obtained was suspended in 10 mM phosphate buffer (pH 7.0), disrupted in usual manner, and centrifuged to obtain an about 4.5 L of a crude enzyme solution. To the solution was added ammonium sulfate to give a saturation of 30 w/v %, salted out by standing it at 4° C. for 4 hours, and centrifuged to obtain a supernatant. Ammonium sulfate was added to the supernatant to give a saturation of 80 w/v %, and allowed to stand it at 4° C. overnight. The resultant sediment was collected by centrifugation, dissolved in a small amount of 10 mM phosphate buffer (pH 7.0), and dialyzed against 10 mM phosphate buffer (pH 7.0) for 24 hours. The dialyzed inner solution was centrifuged to obtain a supernatant which was then applied to a column packed with "DEAE-TOYOPEARL®", a column for ion-exchange chromatography commercialized by Tosoh Corporation, Tokyo, Japan, which had been previously equilibrated with 10 mM phosphate buffer (pH 7.0), followed by feeding to the column a linear gradient buffer of sodium chloride ranging from 0M to 0.4M in 10 mM phosphate buffer (pH 7.0). From the eluate fractions with the objective enzyme activity were collected, pooled, dialyzed against 10 mM phosphate buffer (pH 7.0) containing 1M ammonium sulfate for 10 hours, and centrifuged to obtain a supernatant. The supernatant thus obtained was applied to a column packed with "BUTYL-TOYOPEARL®", a column for hydrophobic chromatography commercialized by Tosoh Corporation, Tokyo, Japan, which had been previously equilibrated with 10 mM phosphate buffer (pH 7.0) containing 1M ammonium sulfate, followed by feeding to the column a linear gradient buffer of ammonium sulfate ranging from 1M to 0M in 10 mM phosphate buffer (pH 7.0). From the eluate fractions with the objective enzyme activity were collected, pooled and applied to a column packed with "MONO Q HR5/5", a column for ion-exchange chromatography commercialized by Pharmacia LKB Biotechnology AB Uppsala, Sweden, which had been previously equilibrated with 10 mM phosphate buffer (pH 7.0), followed by feeding to the column a linear gradient buffer of sodium chloride ranging from 0M to 0.5M, and collecting fractions with the enzyme activity from the eluate. The resultant purified enzyme had a specific activity of about 17 units/mg protein, and the yield was about 46 units per L of the culture.

The purified enzyme was electrophoresed on 7.5 w/v % polyacrylamide gel to give a single protein band with an active enzyme, and this meant that it was considerably-high in purity.

Experiment 2
Physicochemical Property of Enzyme

Experiment 2-1
Action

To an aqueous solution containing 5 w/v % maltose or trehalose as a substrate was added 2 units/g substrate of the purified enzyme obtained in Experiment 1-2, and the mixture was incubated at 20° C. and pH 7.0 for 24 hours. In order to analyze the saccharide composition of the reaction mixture, it was dried in vacuo, dissolved in pyridine, and trimethylsylated in usual manner, and the resultant was subjected to gas chromatography. The equipments and conditions used in this analysis were as follows: "GC-16A" commercialized by Shimadzu Seisakusho, Ltd., Tokyo, Japan, as a gas chromatography a stainless steel column, having an inner diameter of 3 mm and a length of 2 m, packed with 2% "SILICONE OV-17/CHROMOSOLB W" commercialized by GL Sciences Inc., Tokyo, Japan, as a column; a model of hydrogen flame ionization as a detector; nitrogen gas as a carrier gas (flow rate of 40 ml/min); and a column temperature of 160°–320° C. at a programmed temperature rate of 7.5° C./min. The saccharide compositions of the reaction mixtures were tabulated in Table 1:

TABLE 1

| Substrate | Saccharide in reaction mixture | Saccharide composition (W/W %) |
|---|---|---|
| Maltose | Glucose | 4.9 |
|  | Maltose | 22.3 |
|  | Trehalose | 72.8 |
| Trehalose | Glucose | 3.2 |
|  | Maltose | 17.2 |
|  | Trehalose | 79.6 |

As shown in Table 1, the purified enzyme formed about 73 w/w % trehalose and about 5 w/w % maltose when acted on maltose as a substrate, while it formed about 17 w/w % maltose and about 3 w/w % glucose when acted on trehalose as a substrate. These facts indicate that the purified enzyme has activities of converting maltose into trehalose and of converting trehalose into maltose, as well as of hydrolyzing α-1,4 linkage in maltose molecule and α,α-1,1 linkage in trehalose molecule. There has been no report of such an enzyme, and this led to an estimation of having a novel enzymatic pathway.

Experiment 2-2
Molecular Weight

In accordance with the method reported by U. K. Laemmli in *Nature*, Vol.227, pp.680–685 (1970), the purified enzyme was electrophoresed on sodium dodecyl sulfate polyacrylamide gel electrophoresis (SDS-PAGE) to show a single protein band at a position corresponding to about 57,000–67,000 daltons. The marker proteins used in this experiment were myosin (MW=200,000 daltons), β-galactosidase (MW=116,250 daltons), phosphorylase B (MW=97,400 daltons), serum albumin (MW=66,200 daltons) and ovalbumin (MW=45,000 daltons).

Experiment 2-3
Isoelectric Point

The purified enzyme gave an isoelectric point of about 4.1–5.1 when measured on isoelectrophoresis.

Experiment 2-4
Optimum Temperature

The optimum temperature of the purified enzyme was about 20° C. as shown in FIG. 1 when incubated in usual manner in 10 mM phosphate buffer (pH 7.0) for 60 min.

Experiment 2-5
Optimum pH

Figure 2:
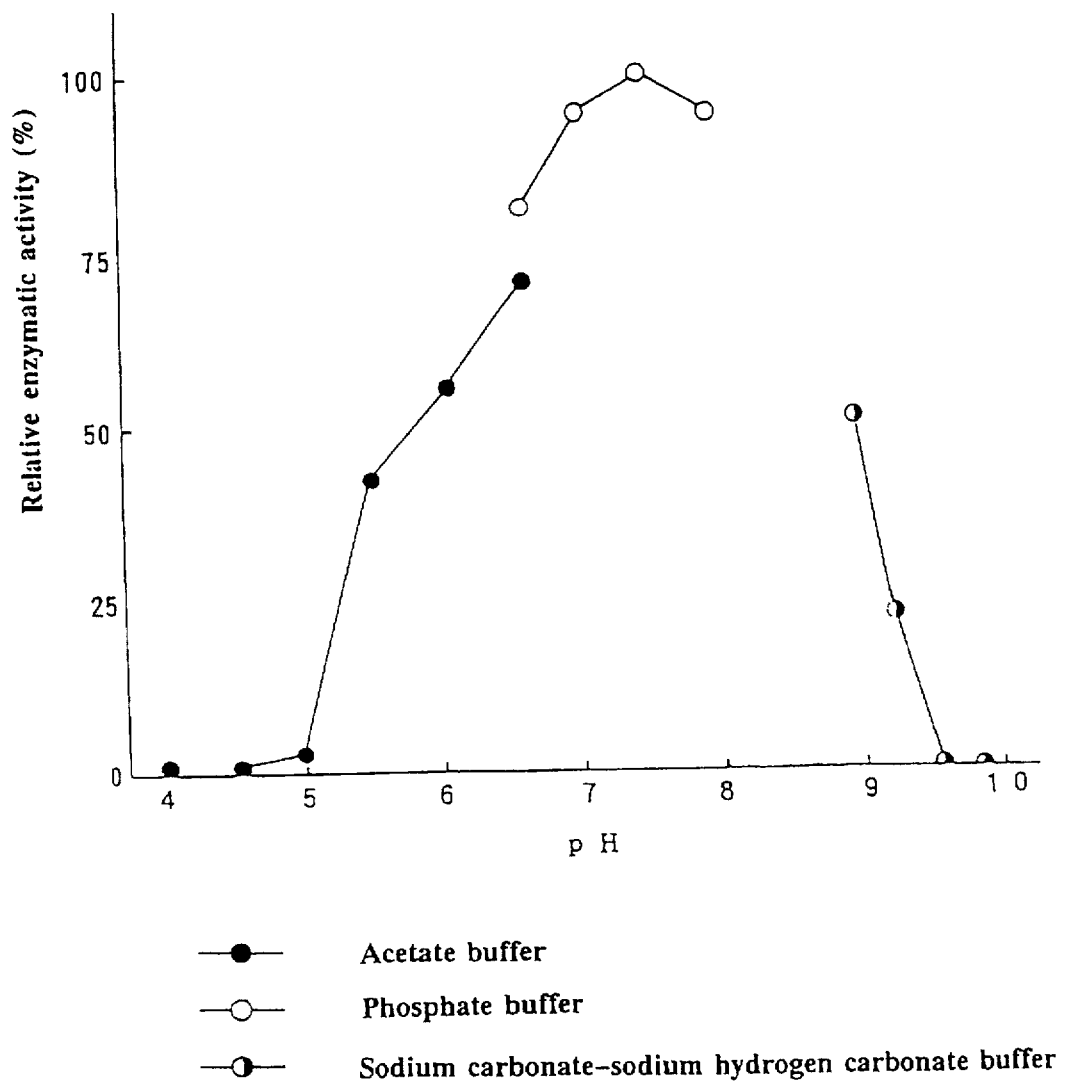
FIG. 2 shows the optimum pH of an enzyme produced by *Pimelobacter sp.* R48.

The optimum pH of the purified enzyme was about 7.0–8.0 as shown in FIG. 2 when experimented in usual manner by incubating it at 25° C. for 60 min in 10 mM acetate buffer, phosphate buffer or sodium carbonate-sodium hydrogen carbonate buffer having different pHs.

Experiment 2-6
Thermal Stability

Figure 3:
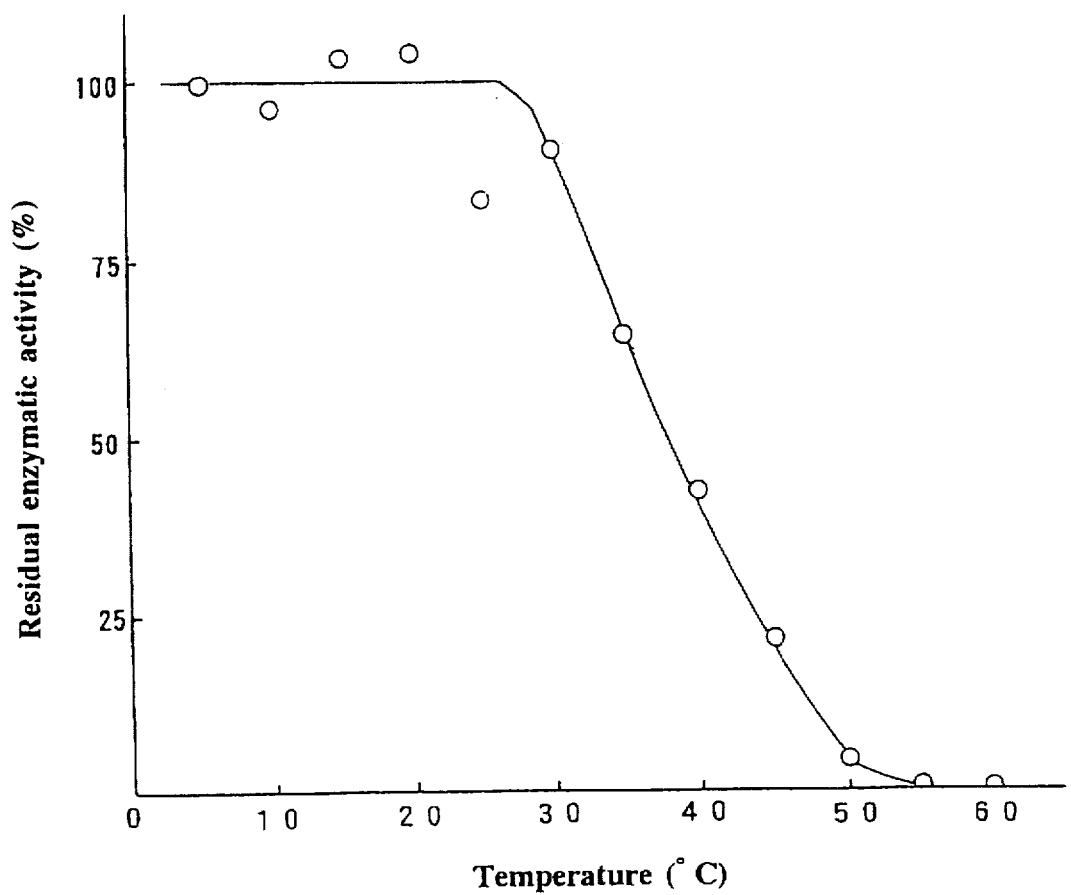
FIG. 3 shows the thermal stability of an enzyme produced by *Pimelobacter sp.* R48.

The purified enzyme was stable up to a temperature of about 30° C. as shown in FIG. 3 when experimented in usual manner by incubating it in 50 mM phosphate buffer (pH 7.0) for 60 min.

Experiment 2-7
pH Stability

Figure 4:
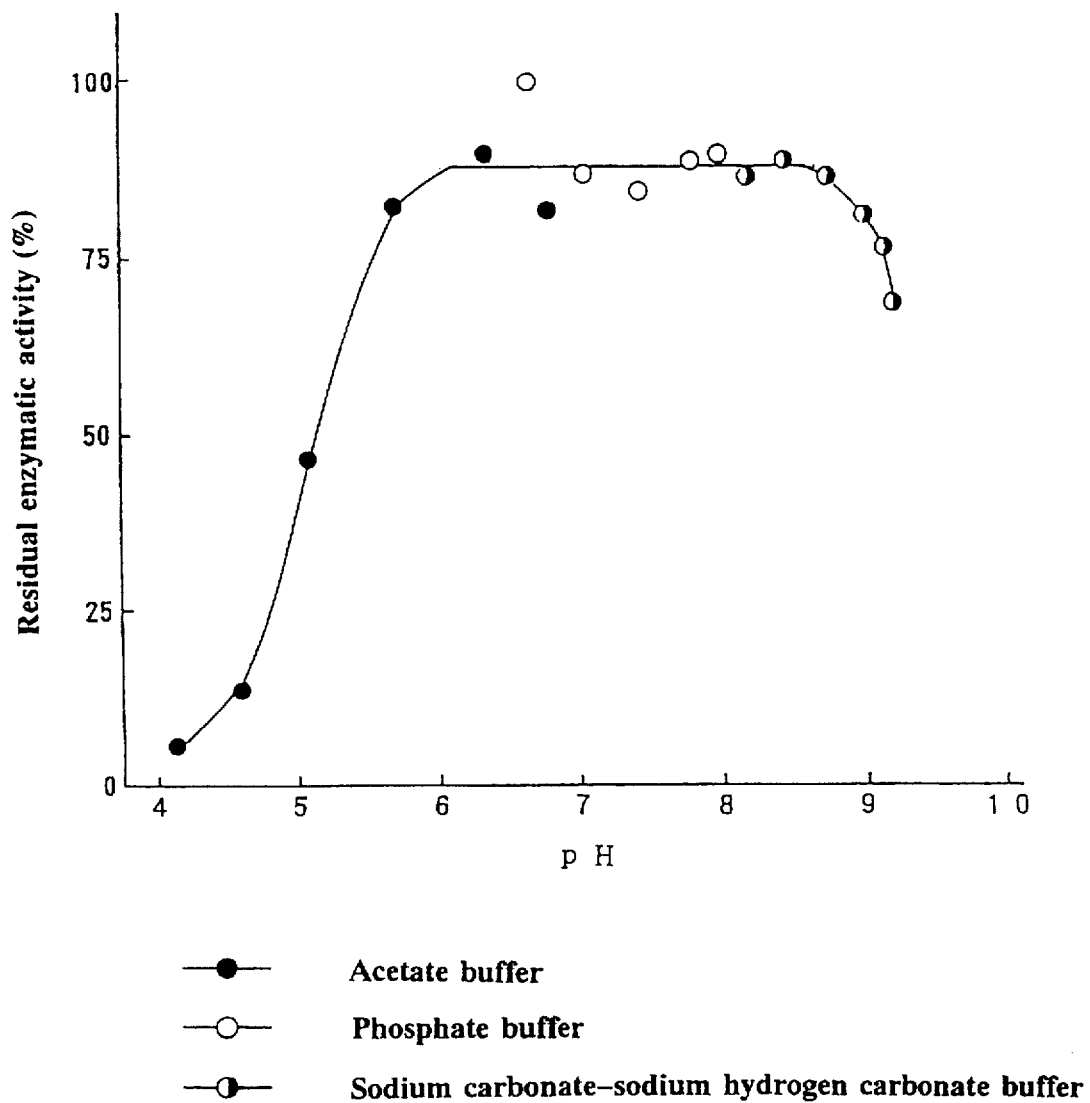
FIG. 4 shows the pH stability of an enzyme produced by *Pimelobacter sp.* R48.

The purified enzyme was stable up to a pH of about 6.0–9.0 as shown in FIG. 4 when experimented in usual manner by incubating it at 20° C. for 60 min in 50 mM acetate buffer, phosphate buffer or sodium carbonate-sodium hydrogen carbonate buffer having different pHs.

Experiment 2-8
Amino Acid Sequence Containing the N-Terminal

The amino acid sequence containing the N-terminal of the purified enzyme was analyzed on "MODEL 470A", a gas-phase protein sequencer commercialized by Perkin-Elmer Corp., Norwalk, USA, to reveal that it has an amino acid sequence containing the N-terminal as shown in SEQ ID NO:3.

Experiment 2-9
Partial Amino Acid Sequence

An adequate amount of the purified enzyme prepared in Experiment 1 was weighed, dialyzed against 10 mM Tris-HCl buffer (pH 9.0) at 4° C. for 18 hours, and admixed with 10 mM Tris-HCl buffer (pH 9.0) to obtain a solution containing about one mg/ml of the enzyme. About one ml of the solution was placed in a test tube, admixed with 10 μg lysyl endopeptidase, and incubated at 30° C. for 22 hours to partially hydrolyze the enzyme. The resultant hydrolysate was applied to "μBONDAPAK C18", a column for reverse-phase high-performance liquid chromatography commercialized by Japan Millipore Ltd., Tokyo, Japan, which had been previously equilibrated with 0.1 v/v % trifluoroacetate containing 16 v/v % aqueous acetonitrile, followed by feeding to the column 0.1 v/v % trifluoroacetate containing acetonitrile at a flow rate of 0.9 ml/min while increasing the concentration of acetonitrile from 16 v/v % to 44 v/v % and separately collecting fractions containing a peptide fragment, eluted about 46 min after the initiation of the feeding. Fractions containing the peptide fragment were pooled, dried in vacuo, and dissolved in 0.1 v/v % trifluoroacetate containing 50 v/v % aqueous acetonitrile. Similarly as in Experiment 2-8, the peptide fragment was analyzed and revealed to have an amino acid sequence as shown in SEQ ID NO:4.

No enzyme having these physicochemical properties has been known, and this concluded that it is a novel substance. Referring to *Pimelobacter sp.* R48, it is a microorganism which was isolated from a soil in Okayama-city, Okayama, Japan, deposited on Jun. 3, 1993, in National Institute of Bioscience and Human-Technology Agency of Industrial Science and Technology, Tsukuba, Ibaraki, Japan, and accepted under the accession number of FERM BP-4315, and it has been maintained by the institute. The bacteriological characteristics of the microorganism are disclosed in detail in Japanese Patent Application No. 199,971/93 applied by the present applicant.

The present inventors energetically screened the chromosomal DNA of *Pimelobacter sp.* R48 by using an oligonucleotide as a probe which had been chemically synthesized based on the amino acid sequence containing the N-terminal and the partial amino acid sequence as revealed in Experiments 2-8 and 2-9, and have obtained a DNA fragment which consists of about 1,700 base pairs having the base sequence as shown in the following SEQ ID NO:2 that initiates from the 5'-terminus. The decoding of the base sequence revealed that it consists of 568 amino acids and has the amino acid sequence that initiates from the N-terminal as shown in SEQ ID NO:1.

The sequential experimental steps, used to reveal the base sequence, and amino acid sequence as shown in SEQ ID NOs:1 and 2 are summarized in the below:

(1) The enzyme was isolated from a culture of a donor microorganism, highly purified, and determined for its amino acid sequence containing the N-terminal. The purified enzyme was partially hydrolyzed with protease, and from which a peptide fragment was isolated and determined for its amino acid sequence;

(2) Separately, a chromosomal DNA was isolated from a donor microorganism's cell, purified and partially digested by a restriction enzyme to obtain a DNA fragment consisting of about 2,000–6,000 base pairs. The DNA fragment was ligated by a DNA ligase to a plasmid vector, which had been previously cut with a restriction enzyme, to obtain a recombinant DNA;

(3) The recombinant DNA was introduced into a microorganism of the species *Escherichia coli* to obtain transformants, and from which an objective transformant containing a DNA encoding the enzyme was selected by the colony hybridization method using an oligonucleotide, as a probe, which had been chemically synthesized based on the aforesaid partial amino acid sequence; and (4) The recombinant DNA was obtained from the selected transformant and annealed with a primer, followed by allowing a DNA polymerase to act on the resultant to extend the primer, and determining the base sequence of the resultant complementary chain DNA by the dideoxy chain termination method. The comparison of an amino acid sequence, which is estimable from the determined base sequence, with the aforesaid amino acid sequence concluded that it encodes the enzyme.

The following Experiments 3 and 4 concretely illustrate the above items (2) to (4), and the techniques used in these experiments were conventional ones commonly used in this field, for example, those described by J. Sumbruck et al. in "*Molecular Cloning A Laboratory Manual*", 2nd edition, published by Cold Spring Harbor Laboratory Press (1989).

Experiment 3
Preparation of Recombinant DNA Containing DNA Derived From *Pimelobacter sp.* R48 and preparation of transformant Experiment 3-1
Preparation of Chromosomal DNA A seed culture of *Pimelobacter sp.* R48 was inoculated into bacto nutrient broth medium (pH 7.0), and cultured at 27° C. for 24 hours with a rotary shaker. The cells were separated from the resultant culture by centrifugation, suspended in TES buffer (pH 8.0), admixed with 0.05 w/v % lysozyme, and incubated at 37° C. for 30 min. The resultant was freezed at −80° C. for one hour, admixed with TSS buffer (pH 9.0), heated to 60° C., and further admixed with a mixture solution of TES buffer and phenol, and the resultant solution was chilled with ice, followed by centrifugation to obtain a supernatant. To the supernatant was added 2-fold volumes of cold ethanol, and the precipitated crude chromosomal DNA was collected, suspended in SSC buffer (pH 7.1), admixed with 7.5 µg ribonuclease and 125 µg protease, and incubated at 37° C. for one hour. Thereafter, a mixture solution of chloroform and isoamyl alcohol was added to the reaction mixture to extract the objective chromosomal DNA, and the extract was admixed with cold ethanol, followed by collecting the formed sediment containing the chromosomal DNA. The resultant purified chromosomal DNA was dissolved in SSC buffer (pH 7.1) to give a concentration of about one mg/ml, and the resultant solution was freezed at −80° C.

Experiment 3-2
Preparation of Recombinant DNA pBRM8 and Transformant BRM8

About one ml of the purified chromosomal DNA obtained in Example 3-1 was placed in a test tube, admixed with about 35 units of Sau 3AI, a restriction enzyme, and enzymatically reacted at 37° C. for about 20 min to partially digest the chromosomal DNA, followed by recovering a DNA fragment consisting of about 2,000–6,000 base pairs by means of sucrose density-gradient ultracentrifugation. One µg of Bluescript II SK(+), a plasmid vector, was placed in a test tube, subjected to the action of Bam HI, a restriction enzyme, to completely digest the plasmid vector, admixed with 10 µg of the DNA fragment and 2 units of T4 DNA ligase, and allowed to stand at 4° C. overnight to ligate the DNA fragment to the plasmid vector fragment. To the resultant recombinant DNA was added 30 µl of "Epicurian Coli®XLI-Blue", a competent cell commercialized by Toyobo Co., Ltd., Tokyo, Japan, allowed to stand under ice-chilling conditions for 30 min, heated to 42° C., admixed with SOC broth, and incubated at 37° C. for one hour to introduce the recombinant DNA into *Escherichia coli*.

The resultant transformant was inoculated into agar plate (pH 7.0) containing 50 µg/ml of 5-bromo-4-chloro-3-indolyl-β-galactoside, and cultured at 37° C. for 18 hours, followed by placing a nylon film on the agar plate to fix thereon about 6,000 colonies formed on the agar plate. Based on the amino acid sequence located at positions from 6 to 11 of SEQ ID NO:1, i.e. Glu-Glu-Pro-Glu-Trp-Phe, the base sequence of probe 1 as shown in SEQ N0:6 was chemically synthesized, labelled with $^{32}$P, and hybridized with the colonies of transformants fixed on the nylon film, followed by selecting 5 transformants which had strongly hybridized with the probe 1.

The objective recombinant DNA was selected in usual manner from the 5 transformants, and, in accordance with the method described by E. M. Southern in *Journal of Molecular Biology*, Vol.98, pp.503–517 (1975), the recombinant DNA was hybridized with probe 2 having the base sequence as shown in SEQ ID NO:7, which had been chemically synthesized based on the amino acid sequence located at positions from 187–192 of SEQ ID NO:1 i.e. Met-Leu-Glu-Ala-Met-Ala, followed by selecting a recombinant DNA which had strongly hybridized with the probe 2. The recombinant DNA and transformant thus selected were respectively named "pBRM8" and "BRM8".

Figure 5:
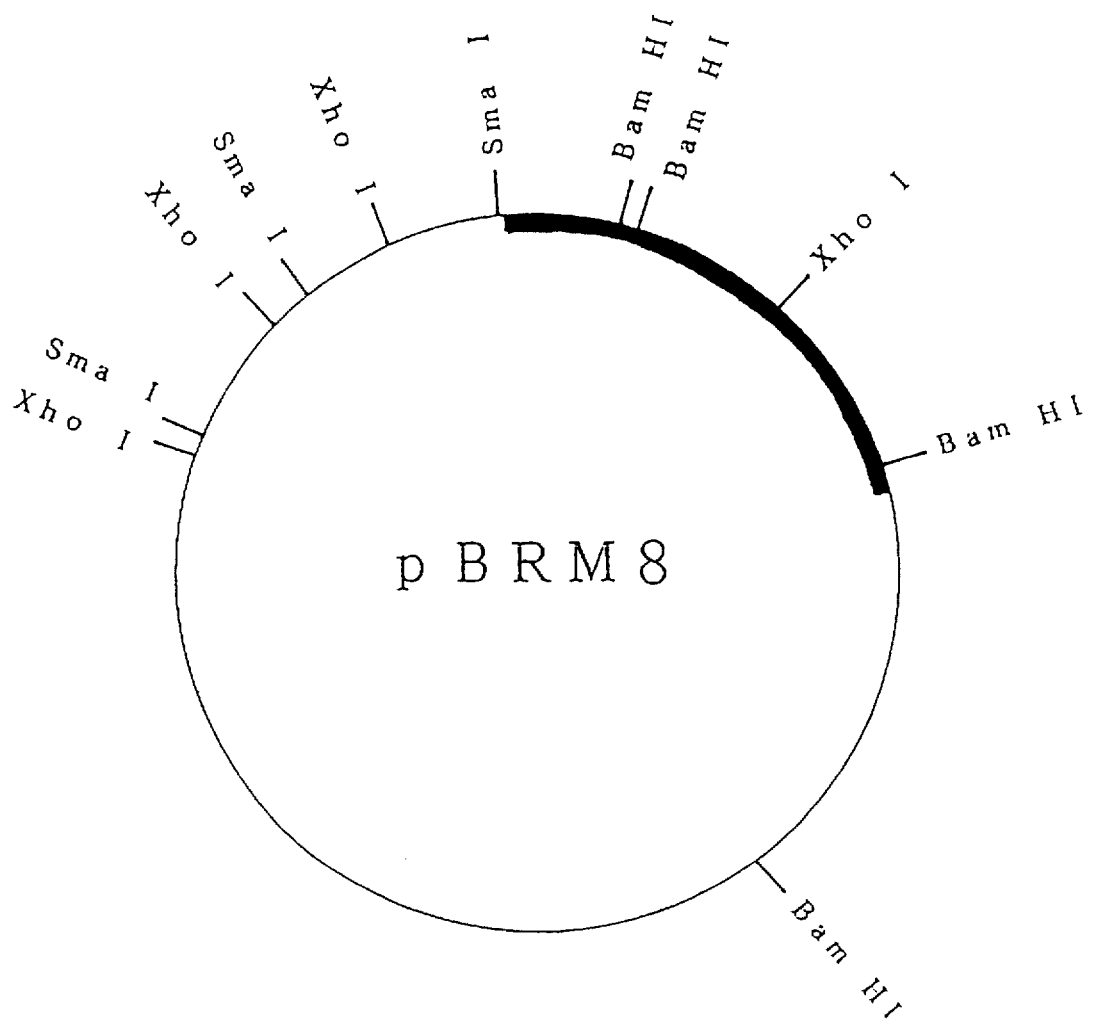
FIG. 5 shows the structure of the recombinant DNA pBRM8 according to the present invention.

The transformant BRM8 was inoculated into L-broth (pH 7.0) containing 100 μg/ml ampicillin, and cultured at 37° C. for 24 hours by a rotary shaker. After completion of the culture, the resultant cells were centrifugally collected from the culture, and treated with the alkaline method in general to extracellularly extract a recombinant DNA. The extract was in usual manner purified and analyzed to reveal that the recombinant DNA pBRM8 consists of about 7,600 base pairs and that as shown in FIG. 5 the DNA, which consists of about 1,700 base pairs and encodes the enzyme, is positioned in the downstream near to the digested site of Sma I, a restriction enzyme.

Experiment 3-3
Production of Recombinant Enzyme by Transformant BRM8

In 500-ml flasks were placed 100 ml aliquots of a liquid nutrient culture medium consisting of 2.0 w/v % glucose, 0.5 w/v % peptone, 0.1 w/v % yeast extract, 0.1 w/v % dipotassium hydrogen phosphate, 0.06 w/v % sodium dihydrogen phosphate, 0.05 w/v % magnesium sulfate heptahydrate, 0.5 w/v % calcium carbonate and water, and each flasks was sterilized by heating at 115° C. for 30 min, cooled, admixed with 50 μg/ml ampicillin, and inoculated with the transformant BRM8 obtained in Experiment 3-2, followed by culturing the transformant at 37° C. for 24 hours by a rotary shaker. The resultant culture was treated with an ultrasonic disintegrator to disrupt cells, and the resultant suspension was centrifuged to remove insoluble substances. The supernatant thus obtained was assayed for the enzyme activity to reveal that one L of the culture contained about 850 units of the enzyme.

As a control, a seed culture of *Escherichia coli* XLI-Blue or *Pimelobacter sp.* R48 was inoculated in a fresh preparation of the same liquid nutrient culture medium but free of ampicillin, and, in the case of culturing *Pimelobacter sp.* R48, it was cultured and treated similarly as above except that the cultivation temperature was set to 27° C. Assaying the resultant activity, one L culture of *Pimelobacter sp.* R48 contained about 410 units of the enzyme, and the yield was significantly lower than that of transformant BRM8. *Escherichia coli* XLI-Blue used as a host did not form the enzyme.

Thereafter, the enzyme produced by the transformant BRM8 was purified similarly as in Experiment 1-2, and examined on its physicochemical properties and characteristics. As a result, it was revealed that it has substantially the same physicochemical properties as the enzyme of *Pimelobacter sp.* R48, i.e. it has a molecular weight of about 57,000–67,000 daltons on SDS-PAGE and an isoelectric point of about 4.1–5.1 on isoelectrophoresis. The results indicate that the present enzyme can be prepared by the recombinant DNA technology, and the yield can be significantly increased thereby.

Experiment 4
Preparation of Complementary Chain DNA and Determination for its Base Sequence and Amino Acid Sequence Two μg of the recombinant DNA pBRM8 obtained in Experiment 3-2 was placed in a test tube, admixed with 2M aqueous sodium hydroxide solution to effect degeneration, and admixed with an adequate amount of cold ethanol, followed by collecting the formed sediment containing a template DNA and drying the sediment in vacuo. To the template DNA were added 50 pmole/ml of a chemically synthesized primer 1 represented by the following SEQ ID NO:8, 10 μl of 40 mM Tris-HCl buffer (pH 7.5) containing 20 mM magnesium chloride and 20 mM sodium chloride, and the mixture was incubated at 65° C. for 2 min to effect annealing and admixed with 2 μl of an aqueous solution containing dATP, dGTP and dTTP in respective amounts of 7.5 μM, 0.5 μl of [α-$^{32}$P]dCTP (2 mCi/ml), one μl of 0.1M dithiothreitol, and 2 μl of 1.5 units/ml T7 DNA polymerase, followed by incubating the resultant mixture at 25° C. for 5 min to extend the primer 1 from the 5'-terminus to the 3'-terminus. Thus, a complementary chain DNA was formed.

The reaction product containing the complementary chain DNA was divided into four equal parts, to each of which 2.5 μl of 50 mM aqueous sodium chloride solution containing 80 μM dNTP and 8 μM ddATP, ddCTP, ddGTP or ddTTP was added, and the resultant mixture was incubated at 37° C. for 5 min, followed by suspending the reaction by the addition of 4 μl of 98 v/v % aqueous formamide solution containing 20 mM EDTA, 0.05 w/v % bromophenol blue, and 0.05 w/v % xylene cyanol. The reaction mixture was heated with a boiling-water bath for 3 min, and a small portion of which was placed on a 6 w/v % polyacrylamide gel, and electrophoresed by energizing it with a constant voltage of about 2,000 volts to separate DNA fragments, followed by fixing the gel in usual manner, drying it and subjecting the resultant to autoradiography.

Analyses of the DNA fragments separated on the radiogram revealed that the complementary chain DNA contains the base sequence consisting of about 1,700 base pairs as shown in SEQ ID NO:5. An amino acid sequence estimable from the base sequence was shown in parallel in SEQ ID NO:5 and compared with the amino acid sequence containing the N-terminal or the partial amino acid sequence, which had been revealed in Experiments 2-8 and 2-9, to reveal that the amino acid sequence containing the N-terminal as shown in Experiment 2-8 corresponded to the amino acid sequence located at positions from 1 to 20 in SEQ ID NO:5, and that the partial amino acid sequence as shown in Experiment 2-9 corresponded to the amino acid sequence located at positions from 183 to 193. These results indicate that the present enzyme has the amino acid sequence as shown in SEQ ID NO:1, and the enzyme of *Pimelobacter sp.* R48 is encoded by the DNA having the base sequence as shown in SEQ ID NO:2.

As is described above, the present inventors found the enzyme which converts maltose into trehalose and vice versa as a result of their long-term research, and it has a specific physicochemical properties differing from conventional enzymes. The present invention aims to prepare a recombinant enzyme by means of recombinant DNA technology. With reference to examples, the process for preparing such a recombinant enzyme and its uses are described in detail.

The recombinant enzyme as referred to in the present invention includes those which are prepared by the recombinant DNA technology and capable of converting maltose into trehalose and vice versa. Usually the present recombinant DNA has a revealed amino acid sequence, e.g. the amino acid sequence as shown in SEQ ID NO:1 or a complementary amino acid to the amino acid sequence. Variants containing amino acid sequences which are homologous to the amino acid sequence of SEQ ID NO:1 can be prepared by replacing one or more amino acids in those in SEQ ID NO:1 with other amino acids without altering the inherent activity of the enzyme. Although even when used the same DNA and it also depends on hosts into which the DNA is introduced, as well as on ingredients and components of nutrient culture media used for culturing transformants, and their cultivation temperature and pH, there may be produced modified enzymes which have the enzymatic activity inherent to the enzyme encoded by the DNA but defect one or more amino acids located in nearness to the N-terminal of the amino acid sequence of SEQ ID NO:1, or have one or more amino acids newly added to the N-terminal by the modification of intracellular enzymes of hosts after the DNA expression. Such variants can be included in the present recombinant enzyme as long as they convert maltose into trehalose and vice versa.

The recombinant enzyme according to the present invention can be obtained from cultures of transformants containing the specific DNA. Transformants usable in the present invention can be obtained by introducing into appropriate hosts the base sequence containing the 5'-terminus as shown in SEQ ID NO:2, homologous base sequences, or complementary base sequences to these base sequences. One or more bases in the above mentioned base sequences may be replaced with other bases by means of degeneracy of genetic code without altering the amino acid sequence which they encode. Needless to say, one or more bases in the base sequence, which encodes the enzyme or their variants, can be readily replaced with other bases to allow the DNA to actually express the enzyme production in hosts.

Any DNA derived from natural resources and those artificially synthesized can be used in the present invention as long as they have the aforementioned base sequences. The natural resources of the DNA according to the present invention are, for example, microorganisms of the genus Pimelobacter, i.e. *Pimelobacter sp.* R48, from which genes containing the present DNA can be obtained. These microorganisms can be inoculated in nutrient culture media and cultured for about 1–3 days under aerobic conditions, and the resultant cells were collected from cultures and subjected to ultrasonication or treated with a cell-wall lysis enzyme such as lysozyme or β-glucanase to extract genes containing the present DNA. In this case, a proteolytic enzyme such as protease can be used in combination with the cell-wall lysis enzyme, and, in the case of treating the cells with ultrasonication, they may be treated in the presence of a surfactant such as sodium dodecyl sulfate (SDS) or treated with freezing and thawing method. The objective DNA is obtainable by treating the resultant with phenol extraction, alcohol sedimentation, centrifugation, protease treatment and/or ribonuclease treatment used in general in this field. To artificially synthesize the DNA according to the present invention, it can be chemically synthesized by using the base sequence as shown in SEQ ID NO:2, or can be obtained in plasmid form by inserting a DNA, which encodes the amino acid sequence as shown in SEQ ID NO:1, into an appropriate self-replicable vector to obtain a recombinant DNA, introducing the recombinant DNA into an appropriate host to obtain a transformant, culturing the transformant, separating the proliferated cells from the resultant culture, and collecting plasmids containing the recombinant DNA from the cells.

Such recombinant DNA is usually introduced in the form of a recombinant DNA into hosts. Generally the recombinant DNA contains the aforesaid DNA and a self-replicable vector and it can be prepared by conventional method with a relative easiness when the material DNA is in hand. Examples of such a vector are plasmid vectors such as pBR322, pUC18, Bluescript II SK(+), pUB110, pTZ4, pC194, pHV14, TRp7, TEp7, pBS7, etc.; and phage vectors such as λgt·λC, λgt·λB, p11, φ1, φ105, etc. Among these plasmid- and phage-vectors, pBR322, pUC18, Bluescript II SK(+), λgt·λC and λgt·λB are satisfactorily used in case that the present DNA should be expressed in *Escherichia coli*, while pUB110, pTZ4, pC194, p11, φ1 and φ105 are satisfactorily used to express the DNA in microorganisms of the genus Bacillus. The plasmid vectors pHV14, TRp7, TEp7 and pBS7 are suitably used when the recombinant DNA is allowed to grow in 2 or more hosts.

The methods used to insert the present DNA into such vectors in the present invention may be conventional ones generally used in this field. A gene containing the present DNA and a self-replicable vector are first digested by a restriction enzyme and/or ultrasonic disintegrator, then the resultant DNA fragments and vector fragments are ligated. To ligate DNA fragments and vectors, firstly they may be annealed if necessary, then subjected to the action of a DNA ligase in vivo or in vitro. The recombinant DNA thus obtained is replicable without substantial limitation by introducing it into an appropriate host, and culturing the resultant transformant.

The recombinant DNA according to the present invention can be introduced into appropriate host microorganisms including *Escherichia coli* and those of the genus Bacillus as well as actinomyces and yeasts. In the case of using *Escherichia coli* as a host, it can be cultured in the presence of the recombinant DNA and calcium ion, while in the case of using the microorganisms of the genus Bacillus the competent cell method and the colony hybridization method can be employed. Desired transformants can be cloned by the colony hybridization method or by culturing a variety of transformants in nutrient culture media containing either maltose or trehalose and selecting transformants which form trehalose or maltose.

The transformants thus obtained extracellularly produce the objective enzyme when cultured in nutrient culture media. Generally, liquid media in general supplemented with carbon sources, nitrogen sources and/or minerals, and, if necessary, further supplemented with a small amount of amino acids and/or vitamins can be used as the nutrient culture media. Examples of the carbon sources are saccharides such as starch, starch hydrolysate, glucose, fructose and sucrose. Examples of the nitrogen sources are organic- and inorganic-substances containing nitrogen such as ammonia, ammonium salts, urea, nitrate, peptone, yeast extract, defatted soy been, corn steep liquor and beef extract. Cultures containing the objective enzyme can be obtained by inoculating the transformants into nutrient culture media, and incubating them at a temperature of 20–50° C. and a pH of 2–9 for about 1–6 days under aerobic aeration-agitation conditions. Such cultures can be used intact as a crude enzyme preparation, and, usually, cells in the cultures can be disrupted with ultrasonic disintegrator and/or cell-wall lysis enzymes prior to use, followed by separating the enzyme from intact cells and cell debris by filtration and/or centrifugation, and purifying the enzyme. The methods used for purifying the enzyme in the invention include conventional ones in general. From cultures intact cells and cell debris are removed and subjected to one or more methods such as concentration, salting out, dialysis, separately sedimentation, gel filtration chromatography, ion-exchange chromatography, hydrophobic chromatography, affinity chromatography, gel electrophoresis and isoelectric point electrophoresis.

As is described above, the present recombinant enzyme exerts a distinct activity of forming trehalose or maltose from maltose or trehalose respectively, and such an activity has not been found in conventional enzymes. Trehalose has a mild and high-quality sweetness and it has a great advantage of being capable of sweetening food products without fear of causing unsatisfactorily coloration and deterioration because it has no reducing residue within the molecule. By using these properties of the present recombinant enzyme, maltose, which could not have been used in some field due to its reducibility, can be converted into useful trehalose with a satisfactory handleability and substantial no reducibility.

Explaining now the present enzymatic conversion method in more detail, the wording "maltose" as referred to in the present invention usually means a saccharide composition containing maltose, and any material or method can be used in the present invention as long as trehalose is formed when the present recombinant enzyme acts thereon or formed thereby. To effectively produce trehalose in an industrial scale, saccharide compositions with a relatively-high maltose content, i.e., usually, about 70 w/w % or more, preferably, about 80 w/w % or more, can be arbitrarily used. Such saccharide compositions can be prepared by conventional methods generally used in this field, for example, those as disclosed in Japanese Patent Publication Nos. 11,437/81 and 17,078/81 wherein β-amylase is allowed to act on gelatinized- or liquefied-starch and separating the formed maltose by separation-sedimentation method or dialysis method, or those as disclosed in Japanese Patent Publication Nos. 13,089/72 and 3,938/79 wherein β-amylase is allowed to act on gelatinized- or liquefied-starch together with a starch debranching enzyme such as isoamylase or pullulanase.

In the enzymatic conversion method according to the present invention, an effective amount of the present recombinant enzyme is allowed to coexist in an aqueous medium containing maltose, followed by keeping the resultant mixture at a prescribed temperature and pH to enzymatically react until the desired amount of trehalose is formed. Although the enzymatic reaction proceeds even at a relatively-low concentration of about 0.1 w/w %, d.s.b., the concentration may be set to about 2 w/w % or more, d.s.b., preferably, about 5–50 w/w %, d.s.b., to proceed the enzymatic conversion method in an industrial scale. The reaction temperature and pH are set within the range which effectively forms maltose without inactivating the recombinant enzyme, i.e. a temperature of about 30° C., preferably, about 4–30° C., and a pH of about 6–9, preferably, about 7–8. The amount of the recombinant enzyme and the reaction time are appropriately set depending on the conditions of the enzymatic reaction. The present enzymatic conversion method effectively converts maltose into trehalose, and the conversion rate reaches up to about 80% or more in some cases.

The reaction mixtures obtainable by the present enzymatic conversion method can be used intact, and, usually, they may be purified prior to use. For example, the reaction mixtures are filtered and centrifuged to remove insoluble substances, and the resultant solutions are decolored with an activated charcoal, desalted and purified with an ion-exchange resin, and concentrated into syrupy products. Depending on use, the syrupy products can be dried in vacuo and spray-dried into solid products. To obtain products substantially consisting of trehalose, the syrupy products are subjected to one or more methods of chromatographies using ion exchangers, activated charcoals or silica gels, fermentation using yeasts, and removal by decomposing reducing saccharides with alkalis. To treat a relatively-large amount of reaction mixtures, ion-exchange chromatographies such as fixed bed-, moving bed-, and pseudo-moving bed-methods as disclosed in Japanese Patent Laid-Open Nos. 23,799/83 and 72,598/88 are arbitrarily used in the invention, and these enable an industrial-scale production of high-trehalose content products, which have been difficult to obtain in large quantities, in a considerably-high yield. The trehalose and saccharide compositions containing trehalose thus obtained can be used in a variety of products which should be avoided from the reducibility of saccharide sweeteners, and therefore, they can be arbitrarily used in food products in general, cosmetics and pharmaceuticals as a sweetener, taste-improving agent, quality-improving agent, stability, filler, adjuvant or excipient.

The following examples explain the preparation of the recombinant enzyme and the enzymatic conversion method of maltose according to the present invention:

EXAMPLE A-1

Preparation of Recombinant Enzyme

To 500-ml Erlenmeyer flasks were added 100 aliquots of a nutrient culture medium consisting of 2.0 w/v % glucose, 0.5 w/v % peptone, 0.1 w/v % yeast extract, 0.1 w/v % dipotassium hydrogen phosphate, 0.06 w/v % sodium dihydrogen phosphate, 0.05 w/v % magnesium sulfate heptahydrate, 0.5 w/v % calcium carbonate and water, and each flask was sterilized by heating it at 115° C. for 30 min, cooled, admixed with 50 µg/ml ampicillin, and inoculated with the transformant BRM8 obtained in Experiment 3-2, followed by the incubation at 37° C. for 24 hours under rotatory-shaking conditions to obtain a seed culture. To 30-L jar fermenters were added 18 L aliquots of a fresh preparation of the same nutrient culture medium, sterilized similarly as above, admixed with 50 µg/ml ampicillin, and inoculated with 1 v/v % of the seed culture, followed by the incubation at 37° C. and a pH of 6–8 for 24 hours under aeration-agitation conditions. The resultant cultures were pooled, treated with ultrasonication to disrupt cells, centrifuged to remove insoluble substances, followed by assaying the enzymatic activity of the resultant supernatant. As a result, one L of the culture contained about 880 units of the recombinant enzyme. The assay of the supernatant conducted by the method in Experiment 1-2 revealed that in this culture was obtained an about 5 ml aqueous solution containing about 160 units/ml of a recombinant enzyme with a specific activity of about 34 units/mg protein.

EXAMPLE B-1

Preparation of Trehalose Syrup by Recombinant Enzyme

Potato starch powder was suspended in water to give a concentration of 10 w/w %, and the suspension was adjusted to pH 5.5, admixed with 2 units/g starch of "SPITASE HS", an α-amylase specimen commercialized by Nagase Biochemicals, Ltd., Kyoto, Japan, and heated at 95° C. to effect gelatinization and liquefaction. Thereafter, the resultant liquefied solution was autoclaved at 120° C. for 20 min to inactivate the remaining enzyme, promptly cooled to 50° C., adjusted to pH 5.0, admixed with 500 units/g starch of an isoamylase specimen commercialized by Hayashibara Biochemical Laboratories, Inc., Okayama, Japan, and 20 units/g starch of a β-amylase specimen commercialized by Nagase Biochemicals, Ltd., Kyoto, Japan, and subjected to an enzymatic reaction at 50° C. for 24 hours to obtain a saccharide solution containing about 92 w/w % maltose, d.s.b. The saccharide solution was heated at 100° C. for 20 min to inactivate the remaining enzyme, cooled to 10° C., adjusted to pH 7.0, admixed with one unit/g starch of the recombinant enzyme obtained in Example A-1, and subjected to an enzymatic reaction for 96 hours. The reaction mixture was heated at 95° C. for 10 min to inactivate the remaining enzyme, cooled, filtered, and, in usual manner, decolored with an activated charcoal, desalted and deionized with an ion-exchange resin, and concentrated to obtain a 70 w/w % syrup in a yield of about 95% to the material starch, d.s.b.

The product contains about 69 w/w % trehalose, d.s.b, and has a relatively-low reducibility because of its DE (dextrose equivalent) 18.2, as well as having a mild sweetness, moderate viscosity and moisture-retaining ability, and these render it arbitrarily useful in a variety of compositions such as food products, cosmetics and pharmaceuticals as a sweetener, taste-improving agent, stabilizer, filler, adjuvant or excipient.

EXAMPLE B-2

Preparation of Trehalose Powder by Recombinant DNA

The reaction mixture obtained in Example B-1 was adjusted to pH 5.0, admixed with 10 units/g starch of "GLUCOZYME", a glucoamylase specimen commercialized by Nagase Biochemicals, Ltd., Kyoto, Japan, and subjected to an enzymatic reaction at 50° C. for 24 hours. The reaction mixture thus obtained was heated to inactivate the remaining enzyme, and, in usual manner, decolored, desalted, purified and subjected to ion-exchange column chromatography using "XT-1016 (polymerization degree of 4%)", a cation exchange resin in $Na^+$-form commercialized by Tokyo Organic Chemical Industries., Ltd., Tokyo, Japan, to increase the trehalose content. More particularly, the ion-exchange resin, previously suspended in water, was packed in 4 jacketed-stainless steel columns with an inner column diameter of 5.4 cm, and the columns were cascaded in series to give a total column length of 20 m. About 5 v/v % of the reaction mixture was fed to the columns while the inner column temperature was keeping at 60° C., and fractionated by feeding to the columns with 60° C. hot water at an SV (space velocity) 0.15, followed by collecting high-trehalose content fractions. The fractions were pooled, and, in usual manner, concentrated, dried in vacuo, and pulverized to obtain a trehalose powder in a yield of about 55% to the material, d.s.b.

The product contained about 97 w/w % trehalose, d.s.b, and has a relatively-low reducing power because of its DE (dextrose equivalent) 18.2, as well as having a mild sweetness, moderate viscosity, and moisture-retaining ability, and these render it arbitrarily useful in a variety of compositions such as food products, cosmetics and pharmaceuticals as a sweetener, taste-improving agent, stabilizer, filler, adjuvant or excipient.

EXAMPLE B-3

Preparation of Crystalline Trehalose Powder by Recombinant Enzyme

A high-trehalose content fraction, obtained by the method in Example B-2, was in usual manner decolored with an activated charcoal, desalted with an ion-exchanger, and concentrated into an about 70 w/w % solution. The concentrate was placed in a crystallizer and gradually cooled while stirring to obtain a massecuite with a crystallization percentage of about 45%. The massecuite was sprayed at a pressure of about 150 kg/cm$^2$ from a nozzle equipped at the top of a drying tower while about 85° C. hot air was blowing downward from the top of the drying tower, about 45° C. hot air was blowing through under a wire-netting conveyer, which was equipped in the basement of the drying tower, to a crystalline powder collected on the conveyer, and the powder was gradually conveying out from the drying tower. Thereafter, the crystalline powder was transferred to an aging tower and aged for 10 hours in the stream of hot air to complete the crystallization and drying. Thus, a hydrous crystalline trehalose powder was obtained in a yield of about 90% to the material, d.s.b.

The product is substantially free from hygroscopicity and readily handleable, and it can be arbitrarily used in a variety compositions such as food products, cosmetics and pharmaceuticals as a sweetener, taste-improving agent, quality-improving agent, stability, filler, adjuvant or excipient.

EXAMPLE B-4

Preparation of Anhydrous Crystalline Trehalose Powder by Recombinant Enzyme A high-trehalose content fraction, obtained by the method in Example B-2, was purified similarly as in Example B-3, and the resultant solution was transferred to a vessel and boiled under a reduced pressure to obtain a syrup with a moisture content of about 3.0 w/w %. The syrup was placed in a crystallizer, admixed with about one w/w % anhydrous crystalline trehalose as a seed crystal, crystallized at 120° C. while stirring, and transferred to a plain aluminum vessel, followed by aging it at 100° C. for 6 hours to form a block. The block thus obtained was pulverized with a cutter, dried by fluidized bed drying to obtain an anhydrous crystalline trehalose powder with a moisture content of about 0.3 w/w % in a yield of about 85% to the material, d.s.b.

The product with a strong dehydrating activity can be arbitrarily used as a desiccant for food products, cosmetics and pharmaceuticals, as well as their materials and intermediates, and also used as a white powdery sweetener with a mild sweetness in food products, cosmetics and pharmaceuticals.

As is described above, the present invention is based on the finding of a novel enzyme which forms trehalose or maltose when acts on maltose or trehalose, and it aims to explore a way to produce such an enzyme in an industrial scale and in a considerably-high yield by the recombinant DNA technology. The enzymatic conversion method according to the present invention attains the conversion of maltose into a saccharide composition containing trehalose, glucose and/or maltose in a considerably-high yield. Trehalose has a mild and high-quality sweetness, and does not have a reducing residue within the molecule, and because of these it can readily sweeten food products in general without fear of causing unsatisfactory coloration and deterioration. The recombinant enzyme with a revealed amino acid sequence can be used with a greater safety for the preparation of trehalose which is premised to be used in food products.

Therefore, the present invention is an useful invention which exerts the aforesaid significant action and effect as well as giving a great contribution to this field.

While the invention has been particularly shown and described with reference to preferred embodiments thereof, it will be understood by those skilled in the art that the foregoing and other changes in form and details can be made therein without departing from the spirit and scope of the invention.

---

We claim:

1. A recombinant enzyme, which contains an amino acid sequence selected from the group consisting of the amino acid sequence of SEQ ID NO:1 and homologous amino acid sequences to the amino acid sequence of SEQ ID NO:1, said homologous amino acid sequences being obtained by either replacing one or more amino acids in the amino acid sequence of SEQ ID NO:1 with other amino acids, or adding or removing one or more amino acids to or from the N-terminal of the amino acid sequence of SEQ ID NO:1, without altering the enzymatic activity of converting maltose into trehalose and vice versa.

2. The enzyme of claim 1, which has the following physicochemical properties:

(1) Action
  capable of converting maltose into trehalose, and vice versa;

(2) Molecular Weight
  about 57,000–67,000 daltons when determined on sodium dodecyl sulfate polyacrylamide gel electrophoresis (SDS-PAGE); and (3) Isoelectric point (pI)
  about 4.1–5.1 when determined on isoelectric point electrophoresis.

3. An isolated DNA encoding the enzyme of claim 1, which has a base sequence selected from the group consisting of the base sequence of SEQ ID NO:2, homologous base sequences to the base sequence of SEQ ID NO:2, and complementary base sequences to these base sequences, said homologous base sequences being obtained by replacing one or more bases in the base sequence of SEQ ID NO:2 with other bases with respect to the degeneracy of the genetic code without altering the amino acid sequence of SEQ ID NO:1.

4. The DNA of claim 3, which originates from a microorganism of the genus Pimelobacter.

5. A replicable recombinant DNA, comprising a self-replicable vector and a DNA encoding the enzyme of claim 1.

6. The recombinant DNA of claim 5, wherein said DNA contains a base sequence selected from the group consisting of the base sequence of SEQ ID NO:2, homologous base sequences to the base sequence of SEQ ID NO:2, and complementary base sequences to these base sequences, said homologous base sequences being obtained by replacing one or more bases in the base sequence of SEQ ID NO:2 with other bases with respect to the degeneracy of the genetic code without altering the amino acid sequence of SEQ ID NO:1.

7. The recombinant DNA of claim 5, wherein said DNA originates from a microorganism of the genus Pimelobacter.

8. The recombinant DNA of claim 5, wherein said self-replicable vector is a plasmid vector.

9. A transformant which is prepared by introducing into a host selected from the group consisting of microorganisms of the of the genera Escherichia and Bacillus a replicable recombinant DNA which comprises a self-replicable vector and a DNA encoding the enzyme of claim 1.

10. The transformant of claim 9, wherein said DNA contains a base sequence selected from the group consisting of the base sequence of SEQ ID NO:2, homologous base sequences to the base sequence of SEQ ID NO:2, and complementary base sequences to these base sequences, said homologous base sequences being obtained by replacing one or more bases in the base sequence of SEQ ID NO:2 with other bases with respect to the degeneracy of the genetic code without altering the amino acid sequence of SEQ ID NO:1.

11. The transformant of claim 9, wherein said DNA originates from a microorganism of the genus Pimelobacter.

12. The transformant of claim 9, wherein said self-replicable vector is a plasmid vector.

13. A process to prepare the enzyme of claim 1, comprising:

expressing DNA encoding the enzyme of claim 1 in culture to produce said enzyme, said DNA containing a base sequence selected from the group consisting of the base sequence of SEQ ID NO:2, homologous base sequences to the base sequence of SEQ ID NO:2, and complementary base sequences to these base sequences, said homologous base sequences prepared by replacing one or more bases in the base sequence of SEQ ID NO:2 with other bases with respect to the degeneracy of the genetic code without altering the amino acid sequence of SEQ ID NO:1; and collecting the enzyme from the resultant culture.

14. The process of claim 13, wherein said self-replicable vector is a plasmid vector.

15. The process of claim 13, wherein the resultant enzyme is collected with one or more members selected from the group consisting of centrifugation, filtration, concentration, salting out, dialysis, fractional sedimentation, ion-exchange chromatography, gel filtration chromatography, hydrophobic chromatography, affinity chromatography, gel electrophoresis and isoelectric point electrophoresis.

16. A method to convert maltose into trehalose, which comprises adding an effective amount of the enzyme of claim 1 to an aqueous medium containing maltose up to 50 w/v % and subjecting the mixture to a maltose/trehalose conversion enzymatic reaction at a temperature of 4°–45° C. and a pH of 5.5–9.0.

17. The method of claim 16, which yields a composition with a maximum trehalose content of about 80 w/v %, on a dry solid basis.

18. A process to prepare trehalose, which comprises reacting the enzyme of claim 1 with maltose to form trehalose.

19. The process as claimed in claim 18, wherein the purity of said maltose is about 70 w/w % or more, on a dry solid basis.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 568 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Ser Thr Val Leu Gly Glu Glu Pro Glu Trp Phe Arg Thr Ala Val Phe
  1               5                  10                  15
Tyr Glu Val Leu Val Arg Ser Phe Arg Asp Pro Asn Ala Gly Gly Thr
             20                  25                  30
Gly Asp Phe Arg Gly Leu Ala Glu Lys Leu Asp Tyr Leu Gln Trp Leu
         35                  40                  45
Gly Val Asp Cys Leu Trp Val Pro Pro Phe Phe Ser Ser Pro Leu Arg
     50                  55                  60
Asp Gly Gly Tyr Asp Val Ala Asp Tyr Thr Gly Ile Leu Pro Glu Ile
 65                  70                  75                  80
Gly Thr Val Glu Asp Phe His Ala Phe Leu Asp Gly Ala His Glu Arg
                 85                  90                  95
Gly Ile Arg Val Ile Ile Asp Phe Val Met Asn His Thr Ser Asp Ala
            100                 105                 110
His Pro Trp Phe Gln Ala Ser Arg Ser Asp Pro Asp Gly Pro Tyr Gly
        115                 120                 125
Asp Phe Tyr Val Trp Ser Asp Thr Asp Glu Leu Tyr Gln Asp Ala Arg
    130                 135                 140
Val Ile Phe Val Asp Thr Glu Pro Ser Asn Trp Thr Trp Asp Gln Thr
145                 150                 155                 160
Arg Gly Gln Tyr Tyr Trp His Arg Phe Phe His His Gln Pro Asp Leu
                165                 170                 175
Asn Phe Asp Asn Pro Lys Val Gln Asp Ala Met Leu Glu Ala Met Ala
            180                 185                 190
Phe Trp Leu Asp Met Gly Leu Asp Gly Phe Arg Leu Asp Ala Val Pro
        195                 200                 205
Tyr Leu Tyr Glu Arg Pro Gly Thr Asn Gly Glu Asn Leu Pro Glu Thr
    210                 215                 220
His Glu Met Leu Lys Arg Val Arg Arg Phe Val Asp Asp Asn Tyr Pro
225                 230                 235                 240
Asp Arg Val Leu Leu Tyr Glu Ala Asn Gln Trp Pro Thr Asp Val Val
                245                 250                 255
Glu Tyr Phe Gly Pro Glu Glu Arg Glu Asp Gly Thr Val Val Gly Pro
            260                 265                 270
Glu Ser His Met Ala Phe His Phe Pro Val Met Pro Arg Ile Phe Met
        275                 280                 285
Ala Val Arg Arg Glu Ser Arg Phe Pro Ile Ser Glu Ile Met Glu Gln
    290                 295                 300
```

| | | | | | | | | | | | | | | |
|---|---|---|---|---|---|---|---|---|---|---|---|---|---|---|
| Thr | Pro | Ala | Ile | Pro | Glu | Gly | Cys | Gln | Trp | Gly | Ile | Phe | Leu | Arg | Asn |
| 305 | | | | 310 | | | | | 315 | | | | | 320 |
| His | Asp | Glu | Leu | Thr | Leu | Glu | Met | Val | Thr | Asp | Glu | Asp | Arg | Asp | Tyr |
| | | | | 325 | | | | | 330 | | | | | 335 | |
| Met | Trp | Gly | Glu | Tyr | Ala | Lys | Asp | Pro | Arg | Met | Lys | Ala | Asn | Ile | Gly |
| | | | 340 | | | | | 345 | | | | | 350 | | |
| Ile | Arg | Arg | Arg | Leu | Ala | Pro | Leu | Leu | Asp | Asn | Asp | Thr | Asn | Gln | Ile |
| | | | 355 | | | | 360 | | | | | 365 | | | |
| Glu | Leu | Phe | Thr | Ala | Leu | Leu | Leu | Ser | Leu | Pro | Gly | Ser | Pro | Val | Leu |
| | | 370 | | | | 375 | | | | | 380 | | | | |
| Tyr | Tyr | Gly | Asp | Glu | Ile | Gly | Met | Gly | Asp | Asn | Ile | Trp | Leu | Gly | Asp |
| 385 | | | | | 390 | | | | | 395 | | | | | 400 |
| Arg | Asp | Gly | Val | Arg | Thr | Pro | Met | Gln | Arg | Thr | Pro | Asp | Arg | Asn | Val |
| | | | | 405 | | | | | 410 | | | | | 415 | |
| Gly | Phe | Ser | Ala | Ala | Thr | Pro | Gly | Lys | Leu | His | Leu | Pro | Thr | Ile | Gln |
| | | | 420 | | | | | 425 | | | | | 430 | | |
| Asp | Pro | Val | Tyr | Gly | Tyr | Gln | Ser | Val | Asn | Val | Glu | Ala | Gln | Leu | Glu |
| | | | 435 | | | | 440 | | | | | 445 | | | |
| Asn | Pro | Ser | Ser | Leu | Leu | His | Trp | Thr | Arg | Arg | Met | Ile | His | Ile | Arg |
| | 450 | | | | | 455 | | | | | 460 | | | | |
| Arg | Gln | Arg | Asp | Ala | Phe | Gly | Leu | Gly | Thr | Phe | Glu | Asp | Leu | Gly | Gly |
| 465 | | | | | 470 | | | | | 475 | | | | | 480 |
| Ser | Asn | Pro | Ala | Val | Leu | Ser | Tyr | Val | Arg | Glu | Leu | Pro | Gly | Asp | Gly |
| | | | | 485 | | | | | 490 | | | | | 495 | |
| Gly | Asp | Asp | Val | Ile | Leu | Cys | Val | Asn | Asn | Leu | Ser | Arg | Phe | Pro | Gln |
| | | | 500 | | | | | 505 | | | | | 510 | | |
| Pro | Val | Glu | Leu | Asp | Leu | Arg | Lys | Tyr | Glu | Gly | Arg | Val | Pro | Val | Glu |
| | | 515 | | | | | 520 | | | | | 525 | | | |
| Leu | Ile | Gly | Gly | Val | Pro | Phe | Pro | Ala | Val | Gly | Glu | Leu | Pro | Tyr | Leu |
| | 530 | | | | | 535 | | | | | 540 | | | | |
| Leu | Thr | Leu | Ser | Gly | His | Gly | Phe | Tyr | Trp | Phe | Arg | Leu | Thr | Asp | Pro |
| 545 | | | | | 550 | | | | | 555 | | | | | 560 |
| Asp | Thr | Thr | Gly | Arg | Pro | Val | Leu | | | | | | | | |
| | | | | 565 | | | | | | | | | | | |

( 2 ) INFORMATION FOR SEQ ID NO:2:

( i ) SEQUENCE CHARACTERISTICS:
        ( A ) LENGTH: 1704 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

```
TCGACCGTCC  TGGGCGAGGA  ACCCGAGTGG  TTCCGCACGG  CGGTCTTCTA  CGAGGTCCTG        60
GTGCGGTCCT  TCCGGGACCC  CAACGCCGGC  GGCACGGGTG  ACTTCCGCGG  CCTGGCGGAG       120
AAGCTCGACT  ACCTGCAGTG  GCTCGGCGTC  GACTGCCTGT  GGGTGCCGCC  GTTCTTCAGC       180
TCGCCGCTGC  GCGACGGCGG  GTACGACGTC  GCCGACTACA  CCGGGATCCT  CCCGGAGATC       240
GGCACGGTCG  AGGACTTCCA  CGCCTTCCTC  GACGGCGCGC  ACGAGCGCGG  GATCCGGGTG       300
ATCATCGACT  TCGTCATGAA  CCACACGAGT  GACGCGCACC  CGTGGTTCCA  GGCCTCCCGC       360
AGCGATCCCG  ACGGCCCGTA  CGGCGACTTC  TACGTCTGGT  CCGACACCGA  CGAGCTCTAC       420
CAGGACGCGC  GGGTGATCTT  CGTCGACACC  GAGCCGTCGA  ACTGGACGTG  GGACCAGACC       480
```

-continued

```
CGCGGCCAGT ACTACTGGCA CCGCTTCTTC CACCACCAGC CCGACCTGAA CTTCGACAAC      540

CCGAAGGTCC AGGACGCCAT GCTGGAGGCG ATGGCGTTCT GGCTCGACAT GGGCCTCGAC      600

GGCTTCCGGC TCGACGCGGT GCCCTACCTC TACGAGCGTC CCGGCACCAA CGGCGAGAAC      660

CTCCCCGAGA CGCACGAGAT GCTCAAGCGG GTGCGGCGCT TCGTCGACGA CAACTACCCC      720

GACCGGGTGC TGCTGTACGA GGCGAACCAG TGGCCGACCG ACGTGGTGGA GTACTTCGGG      780

CCCGAGGAGC GTGAGGACGG CACGGTCGTC GGGCCCGAGA GTCACATGGC CTTCCACTTC      840

CCGGTGATGC CGCGCATCTT CATGGCGGTG CGCCGCGAGT CGCGCTTCCC GATCTCGGAG      900

ATCATGGAGC AGACGCCGGC GATCCCGGAG GGCTGCCAGT GGGGCATCTT CCTGCGCAAC      960

CACGACGAGC TGACCCTCGA GATGGTCACC GACGAGGACC GCGACTACAT GTGGGGCGAG     1020

TACGCCAAGG ACCCCCGCAT GAAGGCCAAC ATCGGCATCC GGCGGCGGCT CGCGCCGCTG     1080

CTCGACAACG ACACGAACCA GATCGAGCTG TTCACCGCGC TGCTGCTGTC GCTGCCCGGC     1140

TCCCCCGTCC TGTACTACGG CGACGAGATC GGCATGGGCG ACAACATCTG GCTCGGTGAC     1200

CGCGACGGCG TGCGTACGCC GATGCAGCGG ACCCCCGACC GCAACGTCGG CTTCTCGGCG     1260

GCCACGCCCG GCAAGCTGCA CCTGCCGACG ATCCAGGACC CGGTCTACGG CTACCAGAGC     1320

GTCAACGTCG AGGCGCAGCT GGAGAACCCC TCCTCGCTGC TGCACTGGAC CCGCCGGATG     1380

ATCCACATCC GCCGCCAGCG CGACGCCTTC GGGCTGGGCA CCTTCGAGGA CCTCGGCGGC     1440

TCGAACCCGG CGGTGCTGTC CTACGTGCGC GAGCTGCCGG GCGACGGGGG CGACGACGTG     1500

ATCCTCTGCG TCAACAACCT GTCCCGCTTC CCGCAGCCGG TCGAGCTCGA CCTCCGGAAG     1560

TACGAGGGCC GGGTACCGGT GGAGCTGATC GGCGGCGTGC CGTTCCCCGC CGTCGGGGAG     1620

CTCCCGTATC TCCTGACGCT CAGCGGGCAC GGCTTCTACT GGTTCCGGCT CACGGATCCG     1680

GACACGACCG GGAGGCCCGT CCTG                                            1704
```

( 2 ) INFORMATION FOR SEQ ID NO:3:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Ser Thr Val Leu Gly Glu Glu Pro Glu Trp Phe Arg Thr Ala Val Phe
 1               5                  10                  15

Tyr Glu Val Leu
            20
```

( 2 ) INFORMATION FOR SEQ ID NO:4:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Val Gln Asp Ala Met Leu Glu Ala Met Ala Phe
 1               5                  10
```

( 2 ) INFORMATION FOR SEQ ID NO:5:

( i ) SEQUENCE CHARACTERISTICS:
    ( A ) LENGTH: 1704 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 1..1704

( x i ) SEQUENCE DESCRIPTION: SEQ ID NO:5:

| TCG | ACC | GTC | CTG | GGC | GAG | GAA | CCC | GAG | TGG | TTC | CGC | ACG | GCG | GTC | TTC | 48 |
| Ser | Thr | Val | Leu | Gly | Glu | Glu | Pro | Glu | Trp | Phe | Arg | Thr | Ala | Val | Phe | |
| 1 | | | | 5 | | | | | 10 | | | | | 15 | | |

| TAC | GAG | GTC | CTG | GTG | CGG | TCC | TTC | CGG | GAC | CCC | AAC | GCC | GGC | GGC | ACG | 96 |
| Tyr | Glu | Val | Leu | Val | Arg | Ser | Phe | Arg | Asp | Pro | Asn | Ala | Gly | Gly | Thr | |
| | | | 20 | | | | | 25 | | | | | 30 | | | |

| GGT | GAC | TTC | CGC | GGC | CTG | GCG | GAG | AAG | CTC | GAC | TAC | CTG | CAG | TGG | CTC | 144 |
| Gly | Asp | Phe | Arg | Gly | Leu | Ala | Glu | Lys | Leu | Asp | Tyr | Leu | Gln | Trp | Leu | |
| | | 35 | | | | | 40 | | | | | 45 | | | | |

| GGC | GTC | GAC | TGC | CTG | TGG | GTG | CCG | CCG | TTC | TTC | AGC | TCG | CCG | CTG | CGC | 192 |
| Gly | Val | Asp | Cys | Leu | Trp | Val | Pro | Pro | Phe | Phe | Ser | Ser | Pro | Leu | Arg | |
| | 50 | | | | | 55 | | | | | 60 | | | | | |

| GAC | GGC | GGG | TAC | GAC | GTC | GCC | GAC | TAC | ACC | GGG | ATC | CTC | CCG | GAG | ATC | 240 |
| Asp | Gly | Gly | Tyr | Asp | Val | Ala | Asp | Tyr | Thr | Gly | Ile | Leu | Pro | Glu | Ile | |
| 65 | | | | | 70 | | | | | 75 | | | | | 80 | |

| GGC | ACG | GTC | GAG | GAC | TTC | CAC | GCC | TTC | CTC | GAC | GGC | GCG | CAC | GAG | CGC | 288 |
| Gly | Thr | Val | Glu | Asp | Phe | His | Ala | Phe | Leu | Asp | Gly | Ala | His | Glu | Arg | |
| | | | | 85 | | | | | 90 | | | | | 95 | | |

| GGG | ATC | CGG | GTG | ATC | ATC | GAC | TTC | GTC | ATG | AAC | CAC | ACG | AGT | GAC | GCG | 336 |
| Gly | Ile | Arg | Val | Ile | Ile | Asp | Phe | Val | Met | Asn | His | Thr | Ser | Asp | Ala | |
| | | | 100 | | | | | 105 | | | | | 110 | | | |

| CAC | CCG | TGG | TTC | CAG | GCC | TCC | CGC | AGC | GAT | CCC | GAC | GGC | CCG | TAC | GGC | 384 |
| His | Pro | Trp | Phe | Gln | Ala | Ser | Arg | Ser | Asp | Pro | Asp | Gly | Pro | Tyr | Gly | |
| | | 115 | | | | | 120 | | | | | 125 | | | | |

| GAC | TTC | TAC | GTC | TGG | TCC | GAC | ACC | GAC | GAG | CTC | TAC | CAG | GAC | GCG | CGG | 432 |
| Asp | Phe | Tyr | Val | Trp | Ser | Asp | Thr | Asp | Glu | Leu | Tyr | Gln | Asp | Ala | Arg | |
| | 130 | | | | | 135 | | | | | 140 | | | | | |

| GTG | ATC | TTC | GTC | GAC | ACC | GAG | CCG | TCG | AAC | TGG | ACG | TGG | GAC | CAG | ACC | 480 |
| Val | Ile | Phe | Val | Asp | Thr | Glu | Pro | Ser | Asn | Trp | Thr | Trp | Asp | Gln | Thr | |
| 145 | | | | | 150 | | | | | 155 | | | | | 160 | |

| CGC | GGC | CAG | TAC | TAC | TGG | CAC | CGC | TTC | TTC | CAC | CAC | CAG | CCC | GAC | CTG | 528 |
| Arg | Gly | Gln | Tyr | Tyr | Trp | His | Arg | Phe | Phe | His | His | Gln | Pro | Asp | Leu | |
| | | | | 165 | | | | | 170 | | | | | 175 | | |

| AAC | TTC | GAC | AAC | CCG | AAG | GTC | CAG | GAC | GCC | ATG | CTG | GAG | GCG | ATG | GCG | 576 |
| Asn | Phe | Asp | Asn | Pro | Lys | Val | Gln | Asp | Ala | Met | Leu | Glu | Ala | Met | Ala | |
| | | | 180 | | | | | 185 | | | | | 190 | | | |

| TTC | TGG | CTC | GAC | ATG | GGC | CTC | GAC | GGC | TTC | CGG | CTC | GAC | GCG | GTG | CCC | 624 |
| Phe | Trp | Leu | Asp | Met | Gly | Leu | Asp | Gly | Phe | Arg | Leu | Asp | Ala | Val | Pro | |
| | | 195 | | | | | 200 | | | | | 205 | | | | |

| TAC | CTC | TAC | GAG | CGT | CCC | GGC | ACC | AAC | GGC | GAG | AAC | CTC | CCC | GAG | ACG | 672 |
| Tyr | Leu | Tyr | Glu | Arg | Pro | Gly | Thr | Asn | Gly | Glu | Asn | Leu | Pro | Glu | Thr | |
| | 210 | | | | | 215 | | | | | 220 | | | | | |

| CAC | GAG | ATG | CTC | AAG | CGG | GTG | CGG | CGC | TTC | GTC | GAC | GAC | AAC | TAC | CCC | 720 |
| His | Glu | Met | Leu | Lys | Arg | Val | Arg | Arg | Phe | Val | Asp | Asp | Asn | Tyr | Pro | |
| 225 | | | | | 230 | | | | | 235 | | | | | 240 | |

| GAC | CGG | GTG | CTG | CTG | TAC | GAG | GCG | AAC | CAG | TGG | CCG | ACC | GAC | GTG | GTG | 768 |
| Asp | Arg | Val | Leu | Leu | Tyr | Glu | Ala | Asn | Gln | Trp | Pro | Thr | Asp | Val | Val | |
| | | | | 245 | | | | | 250 | | | | | 255 | | |

| GAG | TAC | TTC | GGG | CCC | GAG | GAG | CGT | GAG | GAC | GGC | ACG | GTC | GTC | GGG | CCC | 816 |
| Glu | Tyr | Phe | Gly | Pro | Glu | Glu | Arg | Glu | Asp | Gly | Thr | Val | Val | Gly | Pro | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 260 |     |     |     |     | 265 |     |     |     |     | 270 |     |     |      |
| GAG | AGT | CAC | ATG | GCC | TTC | CAC | TTC | CCG | GTG | ATG | CCG | CGC | ATC | TTC | ATG | 864  |
| Glu | Ser | His | Met | Ala | Phe | His | Phe | Pro | Val | Met | Pro | Arg | Ile | Phe | Met |      |
|     |     | 275 |     |     |     | 280 |     |     |     |     | 285 |     |     |     |     |      |
| GCG | GTG | CGC | CGC | GAG | TCG | CGC | TTC | CCG | ATC | TCG | GAG | ATC | ATG | GAG | CAG | 912  |
| Ala | Val | Arg | Arg | Glu | Ser | Arg | Phe | Pro | Ile | Ser | Glu | Ile | Met | Glu | Gln |      |
|     |     | 290 |     |     |     | 295 |     |     |     | 300 |     |     |     |     |     |      |
| ACG | CCG | GCG | ATC | CCG | GAG | GGC | TGC | CAG | TGG | GGC | ATC | TTC | CTG | CGC | AAC | 960  |
| Thr | Pro | Ala | Ile | Pro | Glu | Gly | Cys | Gln | Trp | Gly | Ile | Phe | Leu | Arg | Asn |      |
| 305 |     |     |     |     | 310 |     |     |     |     | 315 |     |     |     |     | 320 |      |
| CAC | GAC | GAG | CTG | ACC | CTC | GAG | ATG | GTC | ACC | GAC | GAG | GAC | CGC | GAC | TAC | 1008 |
| His | Asp | Glu | Leu | Thr | Leu | Glu | Met | Val | Thr | Asp | Glu | Asp | Arg | Asp | Tyr |      |
|     |     |     |     | 325 |     |     |     |     | 330 |     |     |     |     | 335 |     |      |
| ATG | TGG | GGC | GAG | TAC | GCC | AAG | GAC | CCC | CGC | ATG | AAG | GCC | AAC | ATC | GGC | 1056 |
| Met | Trp | Gly | Glu | Tyr | Ala | Lys | Asp | Pro | Arg | Met | Lys | Ala | Asn | Ile | Gly |      |
|     |     |     | 340 |     |     |     |     | 345 |     |     |     |     | 350 |     |     |      |
| ATC | CGG | CGG | CGG | CTC | GCG | CCG | CTC | CTC | GAC | AAC | GAC | ACG | AAC | CAG | ATC | 1104 |
| Ile | Arg | Arg | Arg | Leu | Ala | Pro | Leu | Leu | Asp | Asn | Asp | Thr | Asn | Gln | Ile |      |
|     |     | 355 |     |     |     | 360 |     |     |     |     | 365 |     |     |     |     |      |
| GAG | CTG | TTC | ACC | GCG | CTG | CTG | CTG | TCG | CTG | CCC | GGC | TCC | CCC | GTC | CTG | 1152 |
| Glu | Leu | Phe | Thr | Ala | Leu | Leu | Leu | Ser | Leu | Pro | Gly | Ser | Pro | Val | Leu |      |
|     | 370 |     |     |     |     | 375 |     |     |     |     | 380 |     |     |     |     |      |
| TAC | TAC | GGC | GAC | GAG | ATC | GGC | ATG | GGC | GAC | AAC | ATC | TGG | CTC | GGT | GAC | 1200 |
| Tyr | Tyr | Gly | Asp | Glu | Ile | Gly | Met | Gly | Asp | Asn | Ile | Trp | Leu | Gly | Asp |      |
| 385 |     |     |     |     | 390 |     |     |     |     | 395 |     |     |     |     | 400 |      |
| CGC | GAC | GGC | GTG | CGT | ACG | CCG | ATG | CAG | CGG | ACC | CCC | GAC | CGC | AAC | GTC | 1248 |
| Arg | Asp | Gly | Val | Arg | Thr | Pro | Met | Gln | Arg | Thr | Pro | Asp | Arg | Asn | Val |      |
|     |     |     |     | 405 |     |     |     |     | 410 |     |     |     |     | 415 |     |      |
| GGC | TTC | TCG | GCG | GCC | ACG | CCC | GGC | AAG | CTG | CAC | CTG | CCG | ACG | ATC | CAG | 1296 |
| Gly | Phe | Ser | Ala | Ala | Thr | Pro | Gly | Lys | Leu | His | Leu | Pro | Thr | Ile | Gln |      |
|     |     |     | 420 |     |     |     |     | 425 |     |     |     |     | 430 |     |     |      |
| GAC | CCG | GTC | TAC | GGC | TAC | CAG | AGC | GTC | AAC | GTC | GAG | GCG | CAG | CTG | GAG | 1344 |
| Asp | Pro | Val | Tyr | Gly | Tyr | Gln | Ser | Val | Asn | Val | Glu | Ala | Gln | Leu | Glu |      |
|     |     | 435 |     |     |     |     | 440 |     |     |     |     | 445 |     |     |     |      |
| AAC | CCC | TCC | TCG | CTG | CTG | CAC | TGG | ACC | CGC | CGG | ATG | ATC | CAC | ATC | CGC | 1392 |
| Asn | Pro | Ser | Ser | Leu | Leu | His | Trp | Thr | Arg | Arg | Met | Ile | His | Ile | Arg |      |
|     | 450 |     |     |     |     | 455 |     |     |     |     | 460 |     |     |     |     |      |
| CGC | CAG | CGC | GAC | GCC | TTC | GGG | CTG | GGC | ACC | TTC | GAG | GAC | CTC | GGC | GGC | 1440 |
| Arg | Gln | Arg | Asp | Ala | Phe | Gly | Leu | Gly | Thr | Phe | Glu | Asp | Leu | Gly | Gly |      |
| 465 |     |     |     |     | 470 |     |     |     |     | 475 |     |     |     |     | 480 |      |
| TCG | AAC | CCG | GCG | GTG | CTG | TCC | TAC | GTG | CGC | GAG | CTG | CCG | GGC | GAC | GGG | 1488 |
| Ser | Asn | Pro | Ala | Val | Leu | Ser | Tyr | Val | Arg | Glu | Leu | Pro | Gly | Asp | Gly |      |
|     |     |     |     | 485 |     |     |     |     | 490 |     |     |     |     | 495 |     |      |
| GGC | GAC | GAC | GTG | ATC | CTC | TGC | GTC | AAC | AAC | CTG | TCC | CGC | TTC | CCG | CAG | 1536 |
| Gly | Asp | Asp | Val | Ile | Leu | Cys | Val | Asn | Asn | Leu | Ser | Arg | Phe | Pro | Gln |      |
|     |     |     | 500 |     |     |     |     | 505 |     |     |     |     | 510 |     |     |      |
| CCG | GTC | GAG | CTC | GAC | CTC | CGG | AAG | TAC | GAG | GGC | CGG | GTA | CCG | GTG | GAG | 1584 |
| Pro | Val | Glu | Leu | Asp | Leu | Arg | Lys | Tyr | Glu | Gly | Arg | Val | Pro | Val | Glu |      |
|     |     | 515 |     |     |     |     | 520 |     |     |     |     | 525 |     |     |     |      |
| CTG | ATC | GGC | GGC | GTG | CCG | TTC | CCC | GCC | GTC | GGG | GAG | CTC | CCG | TAT | CTC | 1632 |
| Leu | Ile | Gly | Gly | Val | Pro | Phe | Pro | Ala | Val | Gly | Glu | Leu | Pro | Tyr | Leu |      |
|     |     | 530 |     |     |     | 535 |     |     |     |     | 540 |     |     |     |     |      |
| CTG | ACG | CTC | AGC | GGG | CAC | GGC | TTC | TAC | TGG | TTC | CGG | CTC | ACG | GAT | CCG | 1680 |
| Leu | Thr | Leu | Ser | Gly | His | Gly | Phe | Tyr | Trp | Phe | Arg | Leu | Thr | Asp | Pro |      |
| 545 |     |     |     |     | 550 |     |     |     |     | 555 |     |     |     |     | 560 |      |
| GAC | ACG | ACC | GGG | AGG | CCC | GTC | CTG |     |     |     |     |     |     |     |     | 1704 |
| Asp | Thr | Thr | Gly | Arg | Pro | Val | Leu |     |     |     |     |     |     |     |     |      |
|     |     |     |     | 565 |     |     |     |     |     |     |     |     |     |     |     |      |

( 2 ) INFORMATION FOR SEQ ID NO:6:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:6:

GARGARCCNG ARTGGTT  17

( 2 ) INFORMATION FOR SEQ ID NO:7:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:7:

ATGYTNGARG CNATGGC  17

( 2 ) INFORMATION FOR SEQ ID NO:8:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:8:

GTAAACGAC GGCCAGT  17